United States Patent
Wang et al.

(10) Patent No.: US 9,321,710 B2
(45) Date of Patent: Apr. 26, 2016

(54) PROCESS FOR PRODUCING PHENOL (75) Inventors: Kun Wang, Bridgewater, NJ (US); Roberto Garcia, Easton, PA (US); Jihad M. Dakka, Whitehouse Station, NJ (US); Gabor Kiss, Hampton, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 15 days.

(21) Appl. No.: 14/110,631

(22) PCT Filed: Dec. 15, 2011

(86) PCT No.: PCT/US2011/065059
§ 371 (c)(1),
(2), (4) Date: Dec. 18, 2013

(87) PCT Pub. No.: WO2012/145030
PCT Pub. Date: Oct. 26, 2012

(65) Prior Publication Data
US 2014/0316098 A1    Oct. 23, 2014

Related U.S. Application Data (60) Provisional application No. 61/476,893, filed on Apr. 19, 2011, provisional application No. 61/509,258, filed on Jul. 19, 2011.

(51) Int. Cl.
*C07C 37/08* (2006.01)
*B01J 29/08* (2006.01)
(Continued)

(52) U.S. Cl.
CPC ............... *C07C 37/08* (2013.01); *B01J 29/06* (2013.01); *B01J 29/08* (2013.01); *B01J 29/90* (2013.01);
(Continued)

(58) Field of Classification Search
CPC .................................................. C07C 37/08
USPC .......... 568/798, 385, 376, 717, 730; 540/485; 562/590; 528/332
See application file for complete search history.

(56) References Cited

U.S. PATENT DOCUMENTS 3,821,314 A    6/1974  Arkell et al.
3,959,381 A    5/1976  Arkell et al.
(Continued)

FOREIGN PATENT DOCUMENTS

EP    0 293 032    11/1988
EP    0 492 807     7/1992
(Continued)

OTHER PUBLICATIONS

Meier et al., "Framework type data FAU zeolites", Atlas of zeolites structure types, Jan. 1, 2001, XP55007150, Retrieved from the Internet: URL:http://izasc.ethz.ch/fmi/xsl/IZA-SC/Atlas_pdf/FAU.pdf, retrieved on Sep. 14, 2011.
(Continued)

*Primary Examiner* — Duc Truong
(74) *Attorney, Agent, or Firm* — Stephen A. Baehl (57) ABSTRACT

In a process for producing phenol, a composition comprising an alkylaromatic compound is contacted with an oxygen-containing stream in the presence of an oxidation catalyst comprising a cyclic imide under oxidation conditions effective to oxidize 15 wt % or less of the alkylaromatic compound based upon the total weight of the composition and produce an oxidation product comprising unreacted alkylaromatic compound and alkylaromatic hydroperoxide in a molar ratio of 6:1 to 100:1. Thereafter, at least a portion of the oxidation product is contacted with an acidic molecular sieve catalyst under cleavage conditions effective to convert at least a portion of the alkylaromatic hydroperoxide into phenol and cyclohexanone.

23 Claims, 1 Drawing Sheet

(51) Int. Cl.
| | |
|---|---|
| B01J 29/90 | (2006.01) |
| C07C 2/66 | (2006.01) |
| C07C 45/53 | (2006.01) |
| C07C 4/06 | (2006.01) |
| C07C 5/11 | (2006.01) |
| C07C 407/00 | (2006.01) |
| C07C 5/367 | (2006.01) |
| C07C 6/12 | (2006.01) |
| C07C 7/148 | (2006.01) |
| B01J 35/00 | (2006.01) |
| B01J 29/06 | (2006.01) |
| B01J 31/02 | (2006.01) |
| C07C 37/00 | (2006.01) |
| B01J 23/42 | (2006.01) |
| B01J 23/44 | (2006.01) |
| B01J 29/18 | (2006.01) |
| B01J 29/70 | (2006.01) |
| B01J 29/74 | (2006.01) |

(52) U.S. Cl.
CPC .......... *B01J 31/0247* (2013.01); *B01J 35/0006* (2013.01); *C07C 2/66* (2013.01); *C07C 4/06* (2013.01); *C07C 5/11* (2013.01); *C07C 5/367* (2013.01); *C07C 6/126* (2013.01); *C07C 7/1485* (2013.01); *C07C 45/53* (2013.01); *C07C 407/00* (2013.01); *B01J 23/42* (2013.01); *B01J 23/44* (2013.01); *B01J 29/18* (2013.01); *B01J 29/70* (2013.01); *B01J 29/7007* (2013.01); *B01J 29/7476* (2013.01); *B01J 2229/186* (2013.01); *B01J 2229/42* (2013.01); *B01J 2231/70* (2013.01); *C07C 2101/14* (2013.01); *C07C 2101/16* (2013.01); *C07C 2521/04* (2013.01); *C07C 2521/06* (2013.01); *C07C 2521/12* (2013.01); *C07C 2521/16* (2013.01); *C07C 2523/06* (2013.01); *C07C 2523/14* (2013.01); *C07C 2523/30* (2013.01); *C07C 2523/44* (2013.01); *C07C 2523/46* (2013.01); *C07C 2523/75* (2013.01); *C07C 2523/755* (2013.01); *C07C 2527/053* (2013.01); *C07C 2527/173* (2013.01); *C07C 2529/08* (2013.01); *C07C 2529/18* (2013.01); *C07C 2529/70* (2013.01); *C07C 2529/84* (2013.01); *C07C 2529/85* (2013.01); *C07C 2529/89* (2013.01)

(56) References Cited

U.S. PATENT DOCUMENTS

| | | |
|---|---|---|
| 4,021,490 A | 5/1977 | Hudson |
| 4,230,638 A | 10/1980 | Murtha |
| 4,262,151 A | 4/1981 | Pujado |
| 4,358,618 A | 11/1982 | Sifniades et al. |
| 4,439,409 A | 3/1984 | Puppe et al. |
| 4,480,141 A | 10/1984 | Drake |
| 4,482,757 A | 11/1984 | Drake |
| 4,487,970 A | 12/1984 | Drake |
| 4,490,565 A | 12/1984 | Chang et al. |
| 4,490,566 A | 12/1984 | Chang et al. |
| 4,826,667 A | 5/1989 | Zones et al. |
| 4,870,217 A | 9/1989 | Knifton |
| 4,898,995 A | 2/1990 | Knifton et al. |
| 4,954,325 A | 9/1990 | Rubin et al. |
| 5,236,575 A | 8/1993 | Bennett et al. |
| 5,250,277 A | 10/1993 | Kresge et al. |
| 5,254,751 A | 10/1993 | Zakoshansky |
| 5,362,697 A | 11/1994 | Fung et al. |
| 6,014,018 A | 1/2000 | Wu et al. |
| 6,037,513 A | 3/2000 | Chang et al. |
| 6,049,018 A | 4/2000 | Calabro et al. |
| 6,077,498 A | 6/2000 | Diaz Cabañas et al. |
| 6,169,215 B1 | 1/2001 | Levin et al. |
| 6,284,927 B1 | 9/2001 | Druliner et al. |
| 6,297,406 B1 | 10/2001 | Levin et al. |
| 6,720,462 B2 | 4/2004 | Kuhnle et al. |
| 6,756,030 B1 | 6/2004 | Rohde et al. |
| 6,852,893 B2 | 2/2005 | Kuhnle et al. |
| 7,102,037 B2 | 9/2006 | Levin et al. |
| 2003/0083527 A1 | 5/2003 | Kuhnle et al. |
| 2004/0162446 A1 | 8/2004 | Black |
| 2004/0236152 A1 | 11/2004 | Black et al. |
| 2007/0265476 A1 | 11/2007 | Dakka et al. |
| 2011/0190546 A1 | 8/2011 | Dakka et al. |

FOREIGN PATENT DOCUMENTS

| | | |
|---|---|---|
| GB | 681613 | 11/1950 |
| JP | 2007-009745 | 4/2007 |
| JP | 2007-099746 | 4/2007 |
| WO | WO 97/17290 | 5/1997 |
| WO | 2006/015826 | 2/2006 |
| WO | 2008/128638 | 10/2008 |
| WO | WO 2009/025939 | 2/2009 |
| WO | 2009/058527 | 5/2009 |
| WO | WO 2009/131769 | 10/2009 |
| WO | WO 2010/042261 | 4/2010 |
| WO | WO 2010/098916 | 9/2010 |
| WO | WO 2011/001244 | 1/2011 |
| WO | 2011/031374 | 3/2011 |
| WO | WO 2012/145028 | 10/2012 |
| WO | WO 2012/145029 | 10/2012 |
| WO | WO 2012/145031 | 10/2012 |
| WO | WO 2012/145032 | 10/2012 |

OTHER PUBLICATIONS

Aoki et al., "One-Pot Synthesis of Phenol and Cyclohexanone From Cycloheylbenzene Catalyzed by N-Hydroxyphthalimide (NHPI)", Tetrahedron, 2005, vol. 61, pp. 5219-5222.
Cole et al., "Novel Bronsted Acidic Ionic Liquids and Their Use as Dual Solvent-Catalysts", Journal of the American Chemical Society, 2002, vol. 124, pp. 5962-5963.
Ishii et al., "Recent Progress in Aerobic Oxidation of Hydrocarbons by N-Hydroxyimides", Catalysis Today, 2006, vol. 117, pp. 105-113.
Knifton et al., "Phenol/Acetone Cogeneration Via Solid Acid Catalysis", Applied Catalysis A: General, 1997, vol. 161, pp. 199-211.
Koltunov et al., "Efficient Cleavage of Cumene Hydroperoxide over HUSY Zeolites: The Role of Bronsted Acidity", Applied Catalysis A: General, 2008, vol. 336, pp. 29-34.
Leng et al., "Heteropolyanion-Based Ionic Liquids: Reaction-Induced Self-Separation Catalysts from Esterification", Angew. Chem. Int. Ed., 2009, vol. 48, pp. 168-171.
Maksimov et al., "$WO_3/MO_2$ (M=Zr, Sn, Ti) Heterogeneous Acid Catalysts: Synthesis, Study, and Use in Cumene Hydroperoxide Decomposition", Kinetics and Catalysis, 2006, vol. 47, No. 4, pp. 564-571.
Schmidt et al., "New Developments in the Sunoco/UOP Phenol Technology", presented at the AICHE Spring Meeting, Apr. 2004, New Orleans, LA.
Selvin et al., "Catalytic Decomposition of Cumene Hydroperoxide into Phenol and Acetone", Applied Catalysis A: General, Oct. 5, 2001, vol. 219, pp. 125-129.
Zakoshansky, "Acid-catalytic Cumene Hydroperoxide Cleavage Process in Boiling Acetone Medium", presented at the AICHE Spring Meeting, Mar. 2002, New Orleans, LA.
Wang et al., U.S. Appl. No. 61/476,893, "Process for Producing Phenol", filed Apr. 19, 2011.

PROCESS FOR PRODUCING PHENOL

PRIORITY CLAIM TO RELATED APPLICATIONS

This application is a National Stage Application of International Application No. PCT/US2011/065059 filed Dec. 15, 2011, which claims priority to U.S. Provisional Application Ser. No. 61/476,893 filed Apr. 19, 2011, and U.S. Provisional Application Ser. No. 61/509,258 filed Jul. 19, 2011, the disclosures of which are fully incorporated herein by their reference.

CROSS REFERENCE TO RELATED PATENT APPLICATIONS

This application is related to U.S. application Ser. No. 13/143,975 filed Jan. 25, 2010, now allowed; U.S. Provisional Application Ser. No. 61/502,985 filed Jun. 30, 2011 (2011EM102); U.S. Provisional Application Ser. No. 61/502,979 filed Jun. 30, 2011 (2011EM170); U.S. Provisional Application No. 61/476,893 filed Apr. 19, 2011 (2011EM097); and International Patent Cooperation Treaty Application No. PCT/US2011/065063, filed Dec. 15, 2011.

FIELD

The present invention relates to a process for producing phenol.

BACKGROUND

Phenol is an important product in the chemical industry and is useful in, for example, the production of phenolic resins, bisphenol A, $\epsilon$-caprolactam, adipic acid, and plasticizers.

Currently, the most common route for the production of phenol is the Hock process via cumene. This is a three-step process in which the first step involves alkylation of benzene with propylene in the presence of an acidic catalyst to produce cumene. The second step is oxidation, preferably aerobic oxidation, of the cumene to the corresponding cumene hydroperoxide. The third step is the cleavage of the cumene hydroperoxide generally in the presence of a sulfuric acid catalyst into equimolar amounts of phenol and acetone, a co-product.

It is known that phenol and cyclohexanone can be co-produced by a variation of the Hock process in which cyclohexylbenzene is oxidized to obtain cyclohexylbenzene hydroperoxide and the hydroperoxide is decomposed in the presence of an acid catalyst to the desired phenol and cyclohexanone. Although various methods are available for the production of cyclohexylbenzene, a preferred route is disclosed in U.S. Pat. No. 6,037,513, which discloses that cyclohexylbenzene can be produced by contacting benzene with hydrogen in the presence of a bifunctional catalyst comprising a molecular sieve of the MCM-22 family and at least one hydrogenation metal selected from palladium, ruthenium, nickel, cobalt, and mixtures thereof. The '513 patent also discloses that the resultant cyclohexylbenzene can be oxidized to the corresponding hydroperoxide which is then decomposed to the desired phenol and cyclohexanone co-product.

There are, however, a number of problems associated with producing phenol via cyclohexylbenzene rather than the cumene-based Hock process. Firstly, oxidation of cyclohexylbenzene to cyclohexylbenzene hydroperoxide is much more difficult than oxidation of cumene and requires elevated temperatures and the use of a catalyst, generally a cyclic imide, such as N-hydroxyphthalimide (NHPI), to achieve acceptable rates of conversion. However, cyclic imide catalysts are expensive and, when used using to catalyze the oxidation of cyclohexylbenzene, the selectivity to cyclohexylbenzene hydroperoxide decreases with increasing conversion.

In the conventional cumene-based Hock process, the cleavage catalyst is normally sulfuric acid. However, even for the cleavage of cumene hydroperoxide, there are significant disadvantages of using sulfuric acid as the catalyst: 1) sulfuric acid is corrosive, especially in the presence of water, requiring expensive materials for reactor construction; 2) sulfuric acid needs to be neutralized before product separation and distillation, which requires additional chemicals such as phenate, caustics, or organic amines; and 3) the salt generated from neutralization requires separation and disposal and the waste water needs to be treated. Therefore, there are strong incentives to replace sulfuric acid with a heterogeneous cleavage catalyst that eliminates these drawbacks.

The patent and academic literature is replete with suggestions for replacing sulfuric acid in the cleavage of cumene hydroperoxide. Moreover, although less interest has been focused on the cleavage of cyclohexylbenzene hydroperoxide, International Patent Publication No. WO2011/001244 discloses that cyclohexylbenzene hydroperoxide can be converted to phenol and cyclohexanone in the presence of a variety of homogeneous or heterogeneous acid catalysts selected from Brønsted acids and Lewis acids. Suitable homogeneous catalysts are said to include protic acids selected from sulfuric acid, phosphoric acid, hydrochloric acid, and p-toluenesulfonic acid. Solid Brønsted acids such as those sold under the trade name Amberlyst™ and Lewis acids selected from ferric chloride, zinc chloride, and boron trifluoride are also disclosed. In addition, suitable heterogeneous acids are said to include zeolite beta, zeolite Y, zeolite X, ZSM-5, ZSM-12, and mordenite.

Further, Japan Unexamined Patent Publication 2007-099746 discloses that cycloalkyl benzene hydroperoxides can be cleaved with high selectivity to phenol and cycloalkanone in the presence of montmorillonite, silica-alumina, cationic ion exchange resins, sulfonic acid, perfluorosulfonic acid, and heteropolyacids supported on a carrier. Similarly, Japan Unexamined Patent Publication 2007-099745 discloses that cycloalkyl benzene hydroperoxides can be cleaved with high selectivity to phenol and cycloalkanone in the presence of aluminosilicate zeolites having pore diameter of 0.6 nm or greater, such as zeolite Y and zeolite beta.

However, the replacement of sulfuric acid with heterogeneous cleavage catalysts is not without its attendant problems. Thus, with heterogeneous catalysts, especially in fixed-bed operations, the cleavage feed is to be diluted with cleavage product and recycled, in order to better manage the reaction heat and to control reaction temperature. According to the present invention, it has now been found that, by diluting the cleavage feed with unreacted alkylaromatic compound (e.g., cyclohexylbenzene) from the oxidation step rather than, or in addition to the cleavage products, it is possible to achieve an advantageous integration of heterogeneous catalysis in the cleavage step with a cyclic imide catalyst in the oxidation step. In particular, the oxidation step can be deliberately operated at low conversion, thereby leading to shorter residence times in smaller oxidation reactors, lower levels of and better stability for imide catalyst, and higher selectivity to cyclohexylbenzene hydroperoxide. With this approach, the cyclohexylbenzene hydroperoxide in the cleavage feed is already sufficiently diluted with unreacted cyclohexylbenzene to provide the required heat management in the cleavage reaction. In addition, the low level of cyclohexylbenzene hydroperoxide in the cleavage feed gives the possibility of a single-pass, recycle-free cleavage operation, which can save both capital and operating costs.

SUMMARY

Accordingly, the invention resides in one aspect in a process for producing phenol, the process comprising:

(a) contacting a composition comprising an alkylaromatic compound with an oxygen-containing stream in the presence of an oxidation catalyst comprising a cyclic imide under oxidation conditions effective to oxidize 15 wt % or less of the alkylaromatic compound based upon the total weight of the composition and produce an oxidation product comprising unreacted alkylaromatic compound and alkylaromatic hydroperoxide in a molar ratio of 6:1 to 100:1; and (b) contacting at least a portion of the oxidation product with an acidic molecular sieve catalyst under cleavage conditions effective to convert at least a portion of the alkylaromatic hydroperoxide into phenol and a co-product.

In one embodiment, the alkylaromatic compound is cyclohexylbenzene, the alkylaromatic hydroperoxide is cyclohexylbenzene hydroperoxide and the co-product is cyclohexanone.

In one embodiment, the oxidation product comprises unreacted alkylaromatic compound and alkylaromatic hydroperoxide in a molar ratio of about 8:1 to about 20:1.

Conveniently, the acidic molecular sieve is an aluminosilicate molecular sieve. In one embodiment, the aluminosilicate zeolite has a mesopore volume of greater than or equal to 0.3 cc/g. In one embodiment, the aluminosilicate zeolite has an acid site density of less than or equal to 0.45 millimoles/gram (mmole/g). Conveniently, the aluminosilicate zeolite has a pore size greater than 7 Å and in one embodiment is a FAU type zeolite and especially a FAU type zeolite having a unit cell size less than 24.35 Å.

In a further aspect, the invention resides in a process for producing phenol, the process comprising:

(a) hydroalkylating benzene with hydrogen in the presence of a hydroalkylation catalyst under conditions effective to produce a hydroalkylation reaction product comprising cyclohexylbenzene;

(b) separating at least a portion of the cyclohexylbenzene from the hydroalkylation reaction product;

(c) contacting at least a portion of a composition comprising the cyclohexylbenzene from the separating step (b) with an oxygen-containing stream in the presence of an oxidation catalyst comprising a cyclic amide under oxidation conditions effective to oxidize 15 wt % or less of the cyclohexylbenzene based upon the total weight of the composition and produce an oxidation product comprising unreacted cyclohexylbenzene and cyclohexylbenzene hydroperoxide in a molar ratio of 6:1 to 100:1; and (d) contacting at least a portion of the oxidation product with an acidic molecular sieve catalyst under cleavage conditions effective to convert at least a portion of the cyclohexylbenzene hydroperoxide into phenol and cyclohexanone.

DETAILED DESCRIPTION OF THE EMBODIMENTS

Described herein is a process for producing phenol from an alkylaromatic compound in which the alkylaromatic compound is initially oxidized to alkylaromatic hydroperoxide and the resultant peroxide is cleaved to produce phenol and a co-product. In the present process, the oxidation step is conducted in the presence of an oxidation catalyst comprising a cyclic imide and under conditions effective to oxidize 15 wt % or less of alkylaromatic compound by weight and produce an oxidation product comprising unreacted alkylaromatic compound and alkylaromatic hydroperoxide in a molar ratio of 6:1 to 100:1. In this way, the alkylaromatic hydroperoxide in the feed to the cleavage reaction is already sufficiently diluted with unreacted alkylaromatic compound to allow effective heat management in the cleavage reaction even using a fixed bed of a heterogeneous cleavage catalyst. In addition, the low level of alkylaromatic hydroperoxide in the cleavage feed gives the possibility of a single-pass, recycle-free cleavage operation.

Said alkylaromatic compound has a general formula (II):

(II)

in which $R^1$ and $R^2$ each represent hydrogen or an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group.

In one embodiment, the alkylaromatic compound is cumene, the alkylaromatic hydroperoxide is cumene hydroperoxide and the co-product is acetone.

In another embodiment, the alkylaromatic compound is sec-butylbenzene, the alkylaromatic hydroperoxide is sec-butylbenzene hydroperoxide and the co-product is methyl ethyl ketone.

In a preferred embodiment, the alkylaromatic compound is cyclohexylbenzene, the alkylaromatic hydroperoxide is cyclohexylbenzene hydroperoxide and the co-product is cyclohexanone.

In one preferred embodiment, the present process forms part of an integrated process for producing phenol and cyclohexanone from benzene, in which the benzene is converted to cyclohexylbenzene, the cyclohexylbenzene is then oxidized to cyclohexylbenzene hydroperoxide and the cyclohexylbenzene hydroperoxide is cleaved to produce phenol and cyclohexanone. The present process will therefore now be more particularly described with reference to this preferred embodiment.

Production of the Cyclohexylbenzene

In the initial step of the integrated process starting from benzene, cyclohexylbenzene is produced by reacting the benzene with cyclohexene in the presence of a catalyst having an alkylation function and under conditions to promote the following reaction:

The cyclohexene can be supplied to the reaction zone as a separate feed from the benzene, but normally is produced in situ by selective hydrogenation of the benzene in the presence of a hydrogenation component provided on the catalyst having the alkylation function. The bifunctional catalyst is therefore referred to herein as a hydroalkylation catalyst and overall the hydroalkylation reaction proceeds as follows to produce cyclohexylbenzene (CHB):

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

Hydrogen can be supplied to the hydroalkylation step over a wide range of values, but typically is arranged such that the molar ratio of hydrogen to benzene in the hydroalkylation feed is between about 0.15:1 and about 15:1, such as between about 0.4:1 and about 4:1, for example between about 0.4 and about 0.9:1.

In addition to the benzene and hydrogen, a diluent, which is substantially inert under hydroalkylation conditions, may be supplied to the hydroalkylation reaction. Typically the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, generally the diluent is added in an amount such that the weight ratio of the diluent to the aromatic compound is at least 1:100; for example at least 1:10, but no more than 10:1, typically no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 kPa and about 7,000 kPa, such as between about 500 kPa and about 5,000 kPa.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference.);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one, or more than one, unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49; (b) MCM-56; and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 wt % and about 10 wt %, such as between about 0.1 wt % and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with the molecular sieve. Typically, the catalyst composite is produced by co-pelletization, in which a mixture of the molecular sieve and the metal-containing inorganic oxide are formed into pellets at high pressure (generally about 350 kPa to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica, and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Although the hydroalkylation reaction using an MCM-22 family zeolite catalyst activated by the process described herein is highly selective towards cyclohexylbenzene, the effluent from the hydroalkylation reaction will inevitably contain some dicyclohexylbenzene by-product. Depending on the amount of this dicyclohexylbenzene, it may be desirable to either (a) transalkylate the dicyclohexylbenzene with additional benzene or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, and mordenite. The transalkylation reaction is typically conducted under at least partial liquid phase conditions, which suitably include a temperature of about 100° C. to about 300° C., a pressure of about 800 kPa to about 3500 kPa, a weight hourly space velocity of about 1 hf$^{-1}$ to about 10 hr$^{-1}$ on total feed, and a benzene/dicyclohexylbenzene weight ratio about of 1:1 to about 5:1.

Dealkylation or cracking is also typically effected in a reactor separate from the hydroalkylation reactor, such as a reactive distillation unit, at a temperature of about 150° C. to about 500° C. and a pressure of 15 psig to 500 psig (100 kPa, gauge to 3550 kPa, gauge) over an acid catalyst such as an aluminosilicate, an aluminophosphate, a silicoaluminphosphate, amorphous silica-alumina, an acidic clay, a mixed metal oxide, such as $WO_x/ZrO_2$, phosphoric acid, sulfated zirconia, and mixtures thereof. Generally, the acid catalyst includes at least one aluminosilicate, aluminophosphate or silicoaluminphosphate of the FAU, AEL, AFI, and MWW family. Unlike transalkylation, dealkylation can be conducted in the absence of added benzene, although it may be desirable to add benzene to the dealkylation reaction to reduce coke formation. In this case, the weight ratio of benzene to polyalkylated aromatic compounds in the feed to the dealkylation reaction is typically is from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least a portion of the cyclohexane in the $C_6$-rich stream portion to benzene, which again can be recycled to the hydroalkylation reaction. The dehydrogenation catalyst generally comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium and compounds and mixtures thereof. Typically, the hydrogenation-dehydrogenation component is present in an amount between about 0.1 wt % and about 10 wt % of the catalyst. A suitable inorganic promoter (c) comprises at least one metal or compound thereof selected from Group 1 of the Periodic Table of Elements, such as a potassium compound. Typically, the promoter is present in an amount between about 0.1 wt % and about 5 wt % of the catalyst. Suitable dehydrogenation conditions include a temperature of about 250° C. to about 500° C., a pressure of about atmospheric to about 500 psig (100 kPa to 3550 kPa), a weight hourly space velocity of about 0.2 hr$^{-1}$ to 50 hr$^{-1}$, and a hydrogen to hydrocarbon feed molar ratio of about 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2- methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the $C_{12}$ stream. Similarly, bicyclohexyl (BCH) can lead to separation problems downstream. Thus, at least a portion of the hydroalkylation reaction product may be treated with a catalyst under conditions to remove at least 1,1-methylcyclopentylbenzene and/or bicyclohexyl from the product. The catalyst is generally an acid catalyst, such as an aluminosilicate zeolite, and especially faujasite and the treatment is conducted at a temperature of about 100° C. to about 350° C., such as about 130° C. to about 250° C., for a time of about 0.1 to about 3 hours, such as about 0.1 to about 1 hours. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

The catalytic treatment can be conducted on the direct product of the hydroalkylation reaction or after distillation of the hydroalkylation reaction product to separate the $C_6$ and/or the heavies fraction.

The cyclohexylbenzene product from the hydroalkylation reaction and any downstream reaction to remove the impurities discussed above is separated from the reaction effluent(s) and is fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide. This is accomplished by contacting the cyclohexylbenzene with an oxygen-containing stream, such as air and various derivatives of air. For example, it is possible to use air that has been compressed and filtered to removed particulates, air that has been compressed and cooled to condense and remove water, or air that has been enriched in oxygen above the natural approximately 21 mol % in air through membrane enrichment of air, cryogenic separation of air or other conventional means.

The oxidation is conducted in the presence of a cyclic imide catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, or N-hydroxy-o-benzenedisulphonimide may be used. Preferably, the catalyst is N-hydroxyphthalimide. Another suitable catalyst is N,N',N"-thihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N', N"-trihydroxyisocyanuric acid is employed in an amount between 0.0001 wt % to 15 wt %, such as between 0.001 wt % to 5 wt %, of the cyclohexylbenzene.

Suitable conditions for the oxidation step include a temperature between about 70° C. and about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

The conditions and amount of cyclic imide catalyst selected for the oxidation step are arranged so that 15 wt % or less, such as 10 wt % or less, for example 9 wt % or less, or 8 wt % or less, or 7 wt % or less, or 6 wt % or less, or 5 wt % or less, or from 1-15 wt %, or from 1-10 wt %, or from 2-9 wt %, or from 3-7 wt % of the cyclohexylbenzene in the oxidation feed is oxidized to cyclohexylbenzene hydroperoxide based upon total weight of the feed, and the oxidation product comprises unreacted alkylaromatic compound (e.g., cyclohexylbenzene) and alkylaromatic hydroperoxide (e.g., cyclohexylbenzene hydroperoxide) in a molar ratio of at least 6:1, such as about 8:1 to about 20:1, for example about 6:1 to 100:1, or about 10:1 to about 15:1. As used herein, "unreacted alkylaromatic compound" and "unreacted imide catalyst" mean that portion of the alkylaromatic compound and imide catalyst respectively that was not consumed or otherwise transformed in the oxidation reaction.

In various embodiments, the selectivity of CHB to CHBHP (CHBHP selectivity) is 97% or greater. CHBHP selectivity is calculated by dividing the moles of CHBHP by the total moles of oxidation products formed.

In an embodiment, the oxidation reaction is conducted for a period of less than 5 hours, such as from about 1 to about 4 hours, such as from about 1 to 2 hours, in the presence of the cyclic imide catalyst in an amount less than 1000 ppm, such as less than 700 ppm, such as less than 600 ppm, such as less than 500 ppm, or about 100-1000 ppm, or about 150-800 ppm, or about 170 to 700 ppm, or about 200-600 ppm by weight of the cyclohexylbenzene in the oxidation feed. A suitable temperature for the oxidation step is about 70° C. to about 200° C., such as about 90° C. to about 130° C., and a pressure of about 50 kPa to 10,000 kPa.

The reactor used for the oxidation reaction may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the heat generated in the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

At least a portion of the oxidation reaction effluent is then subjected to a cleavage reaction, either directly or after undergoing prior separation or treatment. For example, all or a fraction of the oxidation effluent may be cooled to cause crystallization of the unreacted imide oxidation catalyst, which can then be separated either by filtration or by scraping from a heat exchanger surface used to effect the crystallization. At least a portion of the resultant oxidation composition reduced or free from imide oxidation catalyst may be subjected to the cleavage reaction.

As another example, all or a fraction of the oxidation effluent may be subjected to water washing and then passage through an adsorbent, such as a 3 Angstrom molecular sieve (i.e., a molecular sieve having a 3 Angstrom pore size), to separate water and other adsorbable compounds, and provide an oxidation composition with reduced water or imide content that may be subjected to the cleavage reaction. Similarly, all or a fraction of the oxidation effluent may undergo a chemically or physically based adsorption, such as passage over a bed of sodium carbonate to remove the imide oxidation catalyst (e.g., NHPI) or other adsorbable components, and provide an oxidation composition reduced in oxidation catalyst or other adsorbable component content that may be subjected to the cleavage reaction. Another possible separation involves contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. An example of separation by basic material treatment is disclosed in International Application No. WO 2009/025939, the entire contents of which are incorporated herein by reference.

In another embodiment, all or a fraction of the oxidation effluent may be contacted with an aluminosilicate zeolite of the FAU type to reduce the amount of unreacted imide catalyst in the effluent by adsorption onto the zeolite. As used herein, "FAU-type zeolite" or "zeolite of the FAU type" means a zeolite having a FAU-type structure as described in the *Atlas of Zeolite Framework Types*, Ch. Baerlocher et al. (6th Ed. 2007). The FAU type zeolite employed to remove the oxidation catalyst may be same as the FAU type zeolite employed in the cleavage reaction, namely having a unit cell size less than 24.35 Å, such as less than 24.30 Å, and the contacting to remove the oxidation catalyst can be conducted prior to or concurrently with the cleavage reaction. Unit cell size is determined by X-ray diffraction as described in ASTM D-3942. The adsorbed imide catalyst can be desorbed from the FAU type zeolite by washing with a polar solvent, such as acetone or cyclohexanone, and recovered by flashing off the solvent and/or by recrystallization. The recovered imide can then be recycled back to the oxidation reaction.

In general, however, the need for removal of unreacted imide catalyst from the oxidation effluent may be obviated, or at least reduced, in the present process by the selection of a molecular sieve catalyst for the cleavage step.

Hydroperoxide Cleavage

The alkylaromatic hydroperoxide may then be cleaved in the presence of a heterogeneous acid catalyst. In one embodiment, cyclohexyl-1-phenyl-1-hydroperoxide is cleaved into phenol and cyclohexanone.

Although any heterogeneous acid catalyst can be employed in the present cleavage reaction, suitable acids include acidic molecular sieves and especially aluminosilicate zeolites. Particularly useful are aluminosilicate zeolites having a mesopore volume (pores in the range of 1.7 to 300 nm) of greater than or equal to 0.3 cc/g as measured by $N_2$ adsorption according to ASTM method D4222-03.

Preferably, the aluminosilicate zeolites have an acid site density of less than or equal to 0.45 mmole/g as measured by temperature programmed ammonium adsorption (TPAA). The acid site density measurement is conducted using Mettler TGA/SDTA 851 thermogravimetric analysis system at ambient pressure. In an embodiment, the aluminosilicate zeolite sample is calcined in flowing air to about 500° C. for about three hours; at least until a constant sample weight is obtained. The temperature of the sample is then reduced in flowing air (helium could also be used) to 250° C. and allowed to equilibrate at this temperature in flowing helium and weighed. After being weighed, the sample is subjected to a number of pulses (about 12 seconds/pulse) of gaseous mixture containing helium and ammonia (10 wt %) until a constant weight is obtained. After each pulse of the gas mixture, the aluminosilicate zeolite sample is flushed with flowing helium for about 3 minutes. About 20 separate pulses of the gas mixture are used in each test. The increase in weight of the sample in terms of mg/g aluminosilicate zeolite based on the aluminosilicate zeolite sample weight after calcination is used to determine the moles of $NH_3$ adsorbed per gram of aluminosilicate zeolite.

Examples of suitable aluminosilicate zeolites include those having a pore size greater than 7 Å, such as zeolite beta, zeolite Y, zeolite X, ZSM-12, and mordenite. In one embodiment, the molecular sieve comprises a FAU type zeolite having a unit cell size less than 24.35 Å, such as less than or equal to 24.30 Å, even less than or equal to 24.25 Å. The zeolite can be used in unbound form or can be combined with a binder, such as silica or alumina, such that the overall catalyst (zeolite plus binder) comprises from about 20 wt % to about 80 wt % of the zeolite.

Generally, the cleavage reaction is conducted under conditions including a temperature of about 20° C. to about 200° C., such as about 40° C. to about 120° C. and a pressure of about 100 kPa to about 2000 kPa, such as about 100 kPa to about 1000 kPa, such that the cleavage reaction mixture is completely or predominantly in the liquid phase during the cleavage reaction.

In various embodiments, the phenol selectivity is 97% or greater and/or the cyclohexanone selectivity is 96% or greater. "Selectivity" here is calculated by dividing moles of product produced (phenol or cyclohexanone) by the moles of CHBHP converted.

The overall yield to phenycyclohexanols is also reduced with the present process for two reasons: 1) selectivity to phenylcyclohexanols is significantly reduced with the low conversion in oxidation; and 2) much less secondary cyclohexylbenzene hydroperoxides are formed in oxidation therefore lower levels of phenylcyclohexanols are formed in the cleavage reaction.

The cleavage reaction can be conducted in a variety of reactor configurations and in a single reactor or in a plurality of reactors. For example, the reaction may be conducted at least a first reactor and a second reactor connected in series, with the first reactor being operated at a temperature of about 20° C. to about 120° C. and a pressure of about 100 kPa to about 500 kPa, and the second reactor being operated at a temperature of about 40° C. to about 180° C. and a pressure of about 100 kPa to about 1000 kPa. The first and second reactors may be the same or different.

In various embodiments, the cleavage reaction is performed as a single-step operation without recycle.

In one embodiment, at least a portion of the cleavage reaction is conducted in a continuous stirred tank reactor (CSTR), with the catalyst being slurried in the cleavage reaction medium. Typically, the catalyst is added in an amount between about 50 wppm and about 20,000 wppm of the cleavage reaction medium. Advantages for this configuration include easy heat management and flexibility to add/withdraw catalyst to maintain conversion as the catalyst deactivates. If peroxide cleavage is performed with a molecular sieve catalyst and with the oxidation product containing the imide catalyst, the latter will adsorb on the molecular sieve, gradually inhibiting its performance. The imide catalyst adsorbed on the molecular sieve can be removed/recovered by recovering the imide-loaded molecular sieve from the cleavage reactor and washing this spent molecular sieve with a polar solvent such as acetone or cyclohexanone to recover its cleavage activity and imide adsorbing capacity. The deactivated molecular sieve can be also regenerated by burning off coke in air. In case the molecular sieve is also used for recovery of the imide catalyst, this air-regeneration is advantageously performed after recovering the imide adsorbed on the molecular sieve. In a slurry cleavage process, the molecular sieve can be regenerated on various schedules. Advantageously, the molecular sieve would be continuously withdrawn from the cleavage reactor, regenerated in an external recycle loop, and then returned into the cleavage reactor. Under such operation regime, a steady state of catalyst activity can be maintained through regeneration and by continuously replacing a fraction of the recycled catalyst with fresh catalyst.

A molecular sieve cleavage catalyst can also be used in a fixed bed plug-flow reactor with or without first removing the imide catalyst from the cleavage feed stream. If the imide catalyst is not removed, the molecular sieve bed adsorbs it, allowing its recovery and recycle to the oxidation process. In such a process design, two or more parallel cleavage reactor trains may be deployed to enable uninterrupted processing of the peroxide feed. Thus, as the molecular sieve becomes saturated with the imide catalyst causing it to deactivate in one reactor train, the cleavage feed is switched to another reactor train that contains fresh or regenerated molecular sieve. The imide-saturated molecular sieve can be rejuvenated off-line by, for example, flushing with a polar solvent such as acetone or cyclohexanone. The imide catalyst recovered can be re-used for oxidation. Any coke on the molecular sieve can then also be removed by burning in air before the regenerated reactor train is returned to cleavage operation to replace the previously operating reactor train that can now be taken off-line for regeneration. This cycle then can be repeated until the molecular sieve in one or more reactor trains can no longer be regenerated to acceptable levels. In such cases, the exhausted molecular sieve can simply be replaced with a fresh charge before returning the train to cleavage operations.

The cleavage reaction mixture may contain a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. The preferred polar solvent is phenol and/or cyclohexanone recycled from the cleavage product after cooling. Generally, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

In one embodiment, the less than 1%, or less than 0.5%, or less than 0.1% of the cyclohexylbenzene hydroperoxide is converted to hexanophenone, and/or less than 1% or less than 0.5% or less than 0.1% of the cyclohexylbenzene hydroperoxide is converted to phenylcyclohexanol.

Since the molar ratio of unreacted cyclohexylbenzene to cyclohexylbenzene hydroperoxide in the cleavage reaction mixture is 6:1 to 100:1, heat generation in the cleavage reaction can readily be handled even in a fixed bed cleavage system. In addition, the low level of cyclohexylbenzene hydroperoxide in the cleavage feed gives the possibility of substantially all the peroxide being cleaved in a single-pass, thereby allowing recycle-free cleavage operation, which can save both capital and operating costs. As used herein "substantially all" means that at least 95% of the peroxide present is cleaved to form phenol and co-product.

The major products of the cleavage reaction are phenol and cyclohexanone, each of which generally comprises about 40 wt % to about 60 wt %, or about 45 wt % to about 55 wt % of the cleavage reaction product, such wt % based on the weight of the cleavage reaction product exclusive of unreacted cyclohexylbenzene and acid catalyst.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam and nylons, such as nylon 6 and nylon 6,6.

The phenol produced through the processes disclosed herein may be used, for example, to produce phenolic resins, bisphenol A, ε-caprolactam, adipic acid, and/or plasticizers.

The invention will now be more particularly described with reference to the following non-limiting examples and the accompanying drawing.

EXAMPLE 1

Figure 1:
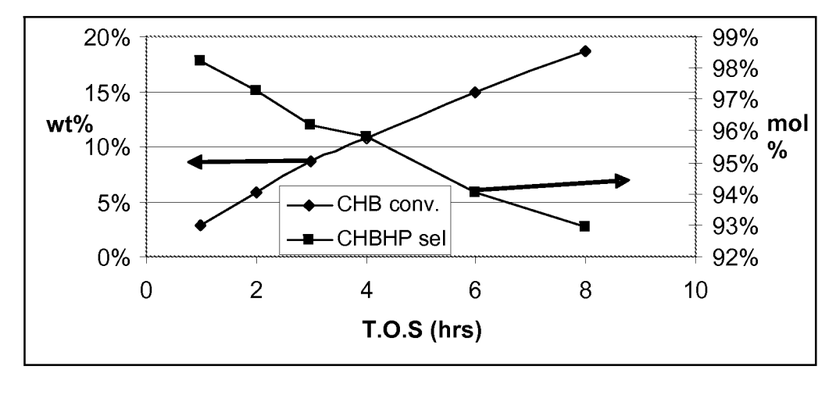
FIG. 1 is a graph showing conversion of CHB and selectivity of CHB to CHBHP against time-on-stream (T.O.S.) in the oxidation process of Example 1.

Oxidation of Cyclohexylbenzene (CHB) Using N-Hydroxyphthalimide (NHPI) as Catalyst 150 g of cyclohexylbenzene from TCI America and 0.16 g NHPI from TCI were weighed into a Parr reactor fitted with a stirrer, thermocouple, gas inlet, sampling port and a condenser containing a Dean-Stark trap for water removal. The reactor contents were stirred at 1000 rpm and sparged with nitrogen at a flow rate of 250 cm$^3$ (cc)/minute for 5 minutes. The reactor, while maintained under a nitrogen sparge was then heated to 105° C. When the reaction temperature was reached, the gas was switched from nitrogen to air and the reactor was sparged with air at 250 cc/minute for 8 hours. Samples were taken and analyzed by gas chromatography. After 8 hours, the gas was switched back to nitrogen and the heat was turned off. The conversion and selectivity profiles are shown in FIG. 1.

EXAMPLE 2

Oxidation of CHB at Lower Conversion and Higher CHBHP Selectivity 150 g of cyclohexylbenzene from TCI America and 0.16 g NHPI from TCI were weighed into a Parr reactor fitted with a stirrer, thermocouple, gas inlet, sampling port, and a condenser containing a Dean-Stark trap for water removal. The reactor contents were stirred at 1000 rpm and sparged with nitrogen at a flow rate of 250 cc/minute for 5 minutes. The reactor, while maintained under a nitrogen sparge was then heated to 105° C. When the reaction temperature was reached, the gas was switched from nitrogen to air and the reactor was sparged with air at 250 cc/minute for 3 hours. Samples were taken and analyzed by gas chromatography. After 3 hours, the gas was switched back to nitrogen and the heat was turned off. The molar ratio of unreacted cyclohexylbenzene to cyclohexylbenzene hydroperoxide in the oxidation product was about 10:1.

EXAMPLE 3

Removal of NHPI from CHB Oxidation Products

An amount of 300 g of the oxidation products from Example 1 was placed in a 500-mL glass flask and mixed with 30 g of anhydrous sodium carbonate (granular form produced by Aldrich). The mixture was stirred overnight and the solid became brick-red in color. The solid was then removed by filtration and the liquid further filtered through a bed of anhydrous magnesium sulfate. A clear, light-yellow liquid was obtained. GC analysis revealed the CHBHP concentration does not change before and after NHPI removal.

EXAMPLE 4

Cleavage of CHBHP Using Faujasite in Fixed-Bed Operation

The CHBHP from Example 3 was diluted with CHB and dodecane to get a feed containing about 5 wt % CHBHP and about 95 wt % CHB. A faujasite catalyst having a silica to alumina molar ratio of 80 was pressed and sized to 20-40 mesh size. An amount of 1 g of the catalyst particles was diluted with quartz chips to 5 cc volume and loaded into the center zone of a ⅜" tubular reactor. The catalyst was first dried with flowing $N_2$ at 200° C. and then temperature cooled down to 60° C. The CHBHP feed was fed to the reactor via an ISCO pump at a liquid pressure of 100 psig (690 kPa, gauge). Cleavage product was collected and analyzed by GC. The results are shown in Table 1.

TABLE 1

| Example | Catalyst (Si/Al$_2$) | WHSV (h$^{-1}$) | CHBHP conv. (%) | Phenol selectivity (%) | Cyclohexanone selectivity (%) |
|---|---|---|---|---|---|
| 4 | CBV780 (80) | 28.5 | 98 | 97 | 96 |

Referring to Table 1, high selectivities to phenol (97%) and cyclohexanone (96%) are obtained with a cleavage feed containing about 5 wt % CHBHP and 95 wt % hydrocarbons such as CHB by using a solid acid catalyst FAU. As shown in FIG. 1, high selectivity to CHBHP (98%) is achieved in oxidation by keeping the conversion of CHB low (about 5 wt %). "CHBHP selectivity" from the oxidation reaction is calculated by dividing the moles of CHBHP by the total moles of oxidation products formed. Therefore, in addition to provide better yields, this improved process can reduce the size of the oxidation reactor. As used herein, "CHBHP conversion" means the amount of CHBHP converted to any product. "Phenol selectivity" or "cyclohexanone selectivity" is calculated by dividing moles of product produced (phenol or cyclohexanone) by the moles of CHBHP converted.

EXAMPLE 5

Batch Mode Cleavage of CHBHP (3 wt %) Using FAU Solid Acid Catalysts

In each of a series of experiments, 30 g of a mixture of CHBHP/CHB/phenol/cyclohexanone (~3/81/8/8 wt. ratio) and dodecane were charged to a 50-mL jacketed glass reactor with a circulating temperature bath. The bath was set to 60° C. and the reactor contents were allowed to equilibrate. Once the temperature had stabilized, a GC sample was taken for the hot feed. 2 wt % of a different FAU catalyst (see Table 2) was then added to each mixture. After a brief reaction exotherm, as indicated by the temperature rise inside the reactor, a 1-mL aliquot was taken at certain time intervals and the solid filtered. The samples generated were analyzed by GC and the results are summarized in Table 2.

TABLE 2

| Catalyst (Si/Al$_2$) | Unit cell size (Å) | Pore volume (cc/g) | TPAA (mmole/g) | Time (min) | CHBHP conv. (%) | Phenol selectivity (%) | Cyclohexanone selectivity (%) |
|---|---|---|---|---|---|---|---|
| CBV400 (5.1) | 24.50 | 0.34 | 0.41 | 60 | 30 | 60 | 27 |
| CBV600 (5.2) | 24.35 | 0.38 | — | 20 | 98 | 93 | 87 |
| CBV720 (30) | 24.28 | 0.49 | 0.38 | 15 | 98 | 96 | 94 |
| CBV760 (60) | 24.24 | 0.51 | 0.28 | 15 | 99 | 96 | 93 |
| CBV780 (80) | 24.24 | 0.5 | 0.08 | 5 | 99 | 96 | 93 |
| HSZ-360 (14) | 24.28 | 0.52 | 0.02 | 5 | 100 | 96 | 92 |
| HSZ-385 (99) | 24.26 | 0.57 | <0.01 | 20 | 97 | 96 | 91 |

The zeolites designated as CBV are available from Zeolyst International, whereas the zeolites designated as HSZ are available from Tosoh Inc.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing phenol, the process comprising:
   (a) contacting a composition comprising an alkylaromatic compound with an oxygen-containing stream in the presence of an oxidation catalyst comprising a cyclic imide under oxidation conditions effective to oxidize 15 wt% or less of the alkylaromatic compound based upon the total weight of the composition and produce an oxidation product comprising unreacted alkylaromatic compound and an alkylaromatic hydroperoxide in a molar ratio of 6:1 to 100:1; and
   (b) contacting at least a portion of the oxidation product with an acidic molecular sieve catalyst under cleavage conditions effective to convert at least a portion of the alkylaromatic hydroperoxide into phenol and a co-product.

2. The process of claim 1, wherein the contacting (a) is conducted for a period of less than 5 hours.

3. The process of claim 1, wherein oxidation product comprises unreacted alkylaromatic compound and alkylaromatic hydroperoxide in a molar ratio of about 8:1 to about 20:1.

4. The process of claim 1, wherein the acidic molecular sieve comprises an aluminosilicate zeolite.

5. The process of claim 4, wherein the aluminosilicate zeolite has a mesopore volume of greater than or equal to 0.3 cc/g.

6. The process of claim 4, wherein the aluminosilicate zeolite has an acid site density of less than or equal to 0.45 mole/g.

7. The process of claim 4, wherein the aluminosilicate zeolite has a pore size greater than 7Å.

8. The process of claim 4, wherein the aluminosilicate zeolite comprises a FAU type zeolite.

9. The process of claim 8, wherein the FAU type zeolite has a unit cell size less than 24.35Å.

10. The process of claim 1, wherein the oxidation conditions are effective to oxidize 1-10 wt% of the alkylaromatic compound, based upon the total weight of the composition.

11. The process of claim 1, wherein the oxidation conditions are effective to oxidize 3-7 wt% of the alkylaromatic compound, based upon the total weight of the composition.

12. The process of claim 1, wherein the cyclic imide is present during the contacting step (a) in an amount less than 1000 ppm by weight of the alkylaromatic compound.

13. The process of claim 1, wherein the alkylaromatic compound is cumene, the alkylaromatic hydroperoxide is cumene hydroperoxide and the co-product is acetone.

14. The process of claim 1, wherein the alkylaromatic compound is sec-butylbenzene, the alkylaromatic hydroperoxide is sec-butylbenzene hydroperoxide, and the co-product is methyl ethyl ketone.

15. The process of claim 1, wherein the alkylaromatic compound is cyclohexylbenzene, the alkylaromatic hydroperoxide is cyclohexylbenzene hydroperoxide, and the co-product is cyclohexanone.

16. The process of claim 1, wherein the phenol is converted to at least one of a phenolic resin, bisphenol A, ε-caprolactam, an adipic acid or a plasticizer.

17. The process of claim 15, wherein the cyclohexanone is converted into at least one of adipic acid, a cyclohexanone resin, a cyclohexanone oxime, caprolactam, or nylon.

18. The process of claim 15, wherein the cyclohexylbenzene hydroperoxide selectivity is 97% or greater.

19. The process of claim 15, wherein the phenol selectivity is 97% or greater and the cyclohexanone selectivity is 96% or greater.

20. The process of claim 1, wherein the contacting step (b) is performed as a single-pass step without recycle.

21. The process of claim 15, wherein substantially all of the cyclohexylbenzene hydroperoxide in the oxidation product portion is converted into phenol and cyclohexanone in a single contacting step.

22. The process of claim 1, further comprising, prior to the contacting (a):
   (a1) hydroalkylating benzene with hydrogen in the presence of a hydroalkylation catalyst under conditions effective to produce a hydroalkylation reaction product comprising cyclohexylbenzene;
   (a2) separating at least a portion of the cyclohexylbenzene from the hydroalkylation reaction product; and
   (a3) supplying the portion of the cyclohexylbenzene from the separating (a2) as the alkylaromatic compound in the contacting (a).

23. The process of claim 22, wherein the acidic molecular sieve catalyst is a FAU type zeolite.

* * * * *